United States Patent
Saikou et al.

(10) Patent No.: US 12,295,549 B2
(45) Date of Patent: May 13, 2025

(54) SURGICAL OPERATION SUPPORT APPARATUS, SURGICAL OPERATION SUPPORT METHOD, AND COMPUTER-READABLE RECORDING MEDIUM

(71) Applicant: NEC Corporation, Tokyo (JP)

(72) Inventors: Masahiro Saikou, Tokyo (JP); Ryuichi Hiraike, Tokyo (JP); Ryosaku Shino, Tokyo (JP)

(73) Assignee: NEC CORPORATION, Tokyo (JP)

( * ) Notice: Subject to any disclaimer, the term of this patent is extended or adjusted under 35 U.S.C. 154(b) by 367 days.

(21) Appl. No.: 17/791,398

(22) PCT Filed: Jan. 21, 2020

(86) PCT No.: PCT/JP2020/002006
§ 371 (c)(1),
(2) Date: Jul. 7, 2022

(87) PCT Pub. No.: WO2021/149169
PCT Pub. Date: Jul. 29, 2021

(65) Prior Publication Data
US 2023/0041542 A1 Feb. 9, 2023

(51) Int. Cl.
*A61B 1/00* (2006.01)
*G06T 7/00* (2017.01)

(52) U.S. Cl.
CPC ...... *A61B 1/00045* (2013.01); *A61B 1/00009* (2013.01); *G06T 7/0012* (2013.01); *G06T 2207/10068* (2013.01)

(58) Field of Classification Search
CPC ............ A61B 1/00045; A61B 1/00009; A61B 1/000094; A61B 1/0005; A61B 1/000095; G06T 7/0012; G06T 2207/10068
See application file for complete search history.

(56) References Cited

U.S. PATENT DOCUMENTS

| | | | |
|---|---|---|---|
| 2017/0371339 A1* | 12/2017 | Charette | B60W 10/20 |
| 2020/0069160 A1 | 3/2020 | Oosake | |
| 2020/0170485 A1 | 6/2020 | Takahashi et al. | |

FOREIGN PATENT DOCUMENTS

| | | | |
|---|---|---|---|
| EP | 3 029 677 | * | 8/2016 |
| JP | H10-201700 A | | 8/1998 |
| JP | 2017-213097 A | | 12/2017 |
| WO | 2016/199273 A1 | | 12/2016 |
| WO | 2017/081976 A1 | | 5/2017 |

(Continued)

OTHER PUBLICATIONS

English translation of Written opinion for PCT Application No. PCT/JP2020/002006, mailed on Aug. 4, 2022.

(Continued)

*Primary Examiner* — Qian Yang

(57) ABSTRACT

A surgical operation support apparatus 1 for performing effective display with respect to a target site image according to the situation has a detection unit 2 that detects a target site image from an image capturing an inside of a living body, an estimation unit 3 that estimates whether the target site image is being observed, and a display information generation unit 4 that generates a first display for facilitating observation of the target site image, if it is estimated that the target site image is being observed.

12 Claims, 7 Drawing Sheets

(56) References Cited

FOREIGN PATENT DOCUMENTS

| WO | 2018/105063 A1 | 6/2018 |
| WO | 2018/216618 A1 | 11/2018 |
| WO | 2018/221033 A1 | 12/2018 |
| WO | 2019/087790 A1 | 5/2019 |

OTHER PUBLICATIONS

Extended European Search Report for EP Application No. 20914888.1, dated on Dec. 9, 2022.
International Search Report for PCT Application No. PCT/JP2020/002006, mailed on Mar. 24, 2020.
Yan Ke et al., "The Design of High-Level Features for Photo Quality Assessment", 2006 IEEE Computer Society Conference on Computer Vision and Pattern Recognition (CVPR'06), New York, NY, USA, Jun. 17-22, 2006.

\* cited by examiner

SURGICAL OPERATION SUPPORT APPARATUS, SURGICAL OPERATION SUPPORT METHOD, AND COMPUTER-READABLE RECORDING MEDIUM

This application is a National Stage Entry of PCT/JP2020/002006 filed on Jan. 21, 2020, the contents of all of which are incorporated herein by reference, in their entirety.

TECHNICAL FIELD

The technical field relates to a surgical operation support apparatus and a surgical operation support method for supporting surgical operations that use an endoscope, and further relates to a computer-readable recording medium including a program recorded thereon for realizing the apparatus and method.

BACKGROUND ART

Surgical operation support apparatuses are known that detect a target site image corresponding to a target site (e.g., lesion region, etc.) from images capturing the inside of a living body using an endoscope, and perform various types of display with respect to the detected target site image to facilitate recognition of the target site image for an observer.

As related technologies, Patent Documents 1 and 2 disclose technologies for performing display that indicates the contour of the target site image and display that fills in the target site image. Also, Patent Document 1 discloses performing display on the target site image, according to the moving speed of a camera provided on the endoscope.

LIST OF RELATED ART DOCUMENTS

Patent Document

Patent Document 1: International Patent Laid-Open Publication No. WO 2018/216618
Patent Document 2: Japanese Patent Laid-Open Publication No. H10-201700

SUMMARY OF INVENTION

Problems to be Solved by the Invention

Patent Documents 1 and 2 are technologies that facilitate recognition of a target site image for an observer, but are not, however, technologies that support observation of the target site image. That is, these are not technologies that enable the target site image to be observed in detail when the target site image is being observed, and facilitate recognition of the target site image in cases other than when the target site image is being observed.

An example of an object of the invention is to provide a surgical operation support apparatus, a surgical operation support method and a computer-readable recording medium for performing effective display with respect to a target site image according to the situation.

Means for Solving the Problems

In order to achieve the above object, a surgical operation support apparatus according to an example aspect of the invention includes:

a detection unit configured to detect a target site image from an image capturing an inside of a living body;

an estimation unit configured to estimate whether the target site image is being observed; and a display information generation unit configured to generate, in a case where it is estimated that the target site image is being observed, a first display for facilitating observation of the target site image.

Also, in order to achieve the above object, a surgical operation support method according to an example aspect of the invention includes:

a detection step of detecting a target site image from an image capturing an inside of a living body;

an estimation step of estimating whether the target site image is being observed; and a display information generation step of generating, in a case where it is estimated that the target site image is being observed, a first display for facilitating observation of the target site image.

Furthermore, in order to achieve the above object, a computer-readable recording medium including a program recorded thereon according to an example aspect of the invention causes a computer to execute:

a detection step of detecting a target site image from an image capturing an inside of a living body;

an estimation step of estimating whether the target site image is being observed; and a display information generation step of generating, in a case where it is estimated that the target site image is being observed, a first display for facilitating observation of the target site image.

Advantageous Effects of the Invention

According to the invention as described above, effective display can be performed with respect to a target site image according to the situation.

EXAMPLE EMBODIMENTS

Example Embodiment

Hereinafter, an example embodiment of the invention will be described with reference to FIGS. 1 to 7.

[Apparatus Configuration]

Figure 1:
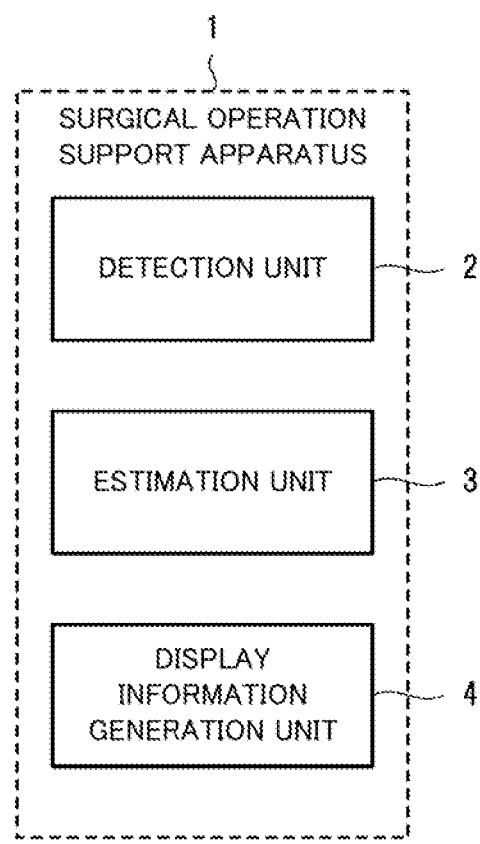
FIG. 1 is a diagram for describing an example of a surgical operation support apparatus 1.

Initially, the configuration of a surgical operation support apparatus 1 in the example embodiment will be described using FIG. 1. FIG. 1 is a diagram for describing an example of the surgical operation support apparatus 1.

The surgical operation support apparatus 1 shown in FIG. 1 is a device that effectively performs display with respect to a target site image according to the situation. Also, as shown in FIG. 1, the surgical operation support apparatus 1 has a detection unit 2, an estimation unit 3 and a display information generation unit 4.

Of these, the detection unit 2 detects a target site image from an image capturing the inside of a living body. The estimation unit 3 estimates whether the target site image is being observed. In the case where it is estimated that the target site image is being observed, the display information generation unit 4 generates a first display for facilitating observation of the target site image.

A specific description will now be given using FIG. 2.

Figure 2:
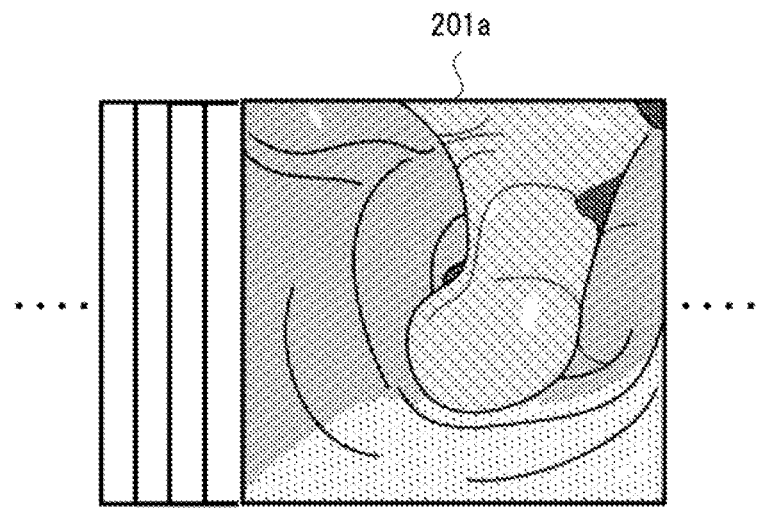
FIG. 2 is a diagram for describing an example of a first display.
Figure 2:
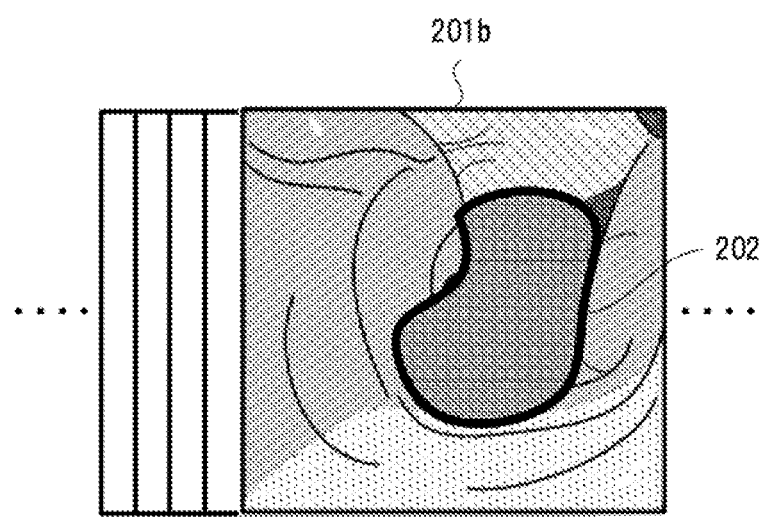
Figure 2:
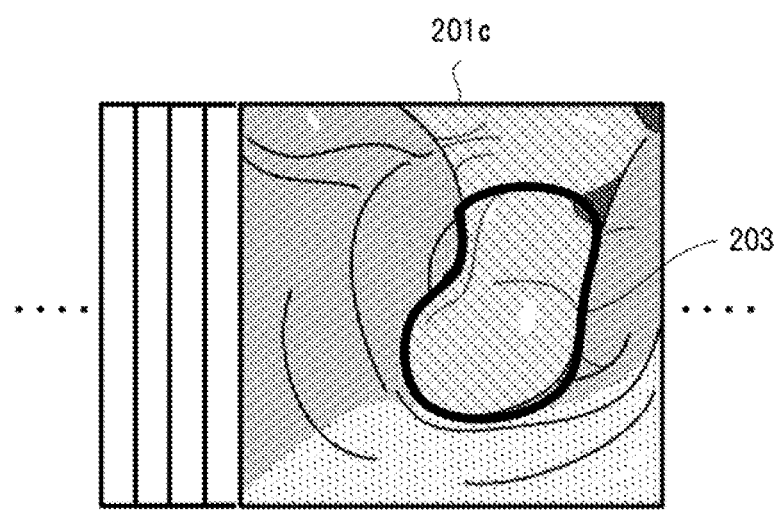

FIG. 2 is a diagram for describing an example of the first display. The detection unit 2 detects a target site image from an image 201a capturing the inside of a living body. The target site is a region inside the body where a lesion (neoplastic lesion, inflammatory lesion, etc.), for example, has occurred. The target site image is an image of the region corresponding to the target site that is included in an image captured by an image capturing apparatus mounted to an endoscope.

Detection of a target site image involves executing segmentation processing on the image 201a capturing the inside of the body and recognizing the region corresponding to the target site. Segmentation processing is described in Document 1, "Hiroshi Fujita, Medical AI and Deep Learning Series—Introduction to Deep Learning for Medical Imaging", "Ohmsha Ltd., Apr. 10, 2019, Chapter 6, and the like.

The estimation unit 3 estimates whether the observer is performing observation. Estimation of whether observation is being performed involves estimating the movement of the image capturing apparatus which is a camera or the like mounted to the endoscope, using one or more images that include the target site image. Whether or not the observer is observing the target site is evident, based on the result of this estimation.

This is because, when the observer is performing observation, the observer keeping the image capturing apparatus as steady as possible, such that the target site image does not move in the images. Accordingly, it is assumed that there will be little evidence of movement of the image capturing apparatus in the images when the observer is performing observation.

In contrast, it is assumed that there will be much evidence of movement of the image capturing apparatus in the images in cases other than when the observer is performing observation. In view of this, the movement of the image capturing apparatus is indexed, by means such as using the degree of bokeh/blur of the image, or the processing result of optical flow processing, or both thereof, for example. It is then determined whether the observer is performing observation, based on these indices.

Estimation of whether observation is being performed is based on the degree of bokeh/blur of the image 201a, for example. Calculation of the degree of bokeh/blur is, for example, described in Document 2: Yan Ke, Xiaoou Tang, Feng Jing, "The Design of High-Level Features for Photo Quality Assessment," School of Computer Science, Carnegie Mellon, Microsoft Research Asia CVPR 2006, 4.1. Spatial Distribution of Edges, 4.4. Blur (https://www.cs.cmu.edu/~yke/photoqual/cvpr06photo.pdf).

Alternatively, estimation of whether observation is being performed involves executing optical flow processing using a plurality of images including the image 201a and performing estimation based on the processing result (amount of movement of the target site image). Optical flow processing is, for example, described in Document 3: Hironobu Fujiyoshi, "Forest of Knowledge" (http://www.ieice-hbkb.org/), IEICE, September 2010, 4-1: "Optical Flow", 4-2: "Tracking" in Chapter 4 "Video Analysis" (http://ieicehbkb.org/files/02/02gun_02hen_04.pdf) in Section 2, Part 2: "Pattern Recognition and Vision".

Alternatively, estimation of whether observation is being performed involves inputting the degree of image bokeh/blur, or the processing result of optical flow processing, or both thereof into a model for classifying whether observation is being performed, for example. Classification of whether observation is being performed can be realized by using various pattern recognition models such as a neural network.

Description is, for example, given in "https://ja.wikipedia.org/wiki/%E3%83%91%E3%82%BF%E3%83%BC%E3%83%B3%E8%AA%8D%E8%AD%98". Also, neural networks are, for example, described in Document 4: Yotaro Kubo, "Pattern Recognition with Deep Learning" (https://ipsj.ixsq.nii.ac.jp/ej/?action=repository_uri&item_id=91504&file_id=1&file_no=1), Journal of Information Processing Society of Japan "Information Processing", Vol. 54, No. 5, May 2013.

If it is estimated by the estimation unit 3 that the observer is observing the target site image, the display information generation unit 4 generates first display information for displaying, on the screen of an output device, a first display for facilitating observation of the target site image. For example, information for displaying a display 203 (solid line area) showing the outline of the target site image shown in an image 201c in FIG. 2 is generated and transmitted to the output device.

Note that the first display is display indicating, in a predetermined color, a surrounding frame surrounding the contour of the target site image, or a surrounding frame entirely including the contour of the target site image, or a surrounding frame surrounding a partial region of the target site image. Note that the shape of the surrounding frame may be elliptical, circular or rectangular, for example. Also, the type of surrounding frame is not limited to a solid line, and may be a dashed line, for example.

Also, if it is estimated to be other than a situation where the target site image is being observed, the display information generation unit 4 generates second display information for displaying, on the screen of the output device, a second display for facilitating recognition of the target site image. For example, information for displaying a display 202 (shaded area) in which the region inside the target site region shown in an image 201b is filled in with a predetermined color or pattern is generated and transmitted to the output device 23.

Note that the second display is display in which the region of the target site image, or a region including the target site image, or a partial region of the target site image is filled in with a predetermined color or pattern.

In this way, in the example embodiment, effective display is performed in the case where it is estimated that the observer is observing the target site image, thus enabling observation of the target site image to be facilitated for the observer.

Specifically, as a method for conveying detection results automatically in the case where a surgeon (observer) who is performing an endoscopic surgical operation observes a lesion, display (display 202) that masks the vascular structure of the lesion region inhibits observation of the lesion by the surgeon, and thus display (display 203) indicating the outline of the lesion is desirable. In contrast, in situations other than when observing a lesion, such as in the case of looking for lesions while removing the endoscope or changing the angle of the camera in order to observe a lesion, for example, display (display 202) that enables the position of the lesion to be easily grasped is desirable.

Note that, in the case where the target site image is being observed, switching to display that facilitates observation of the target site image may be performed automatically as described above, but a configuration may also be adopted in which the observer is able to switch display manually. For example, a configuration may be adopted in which a switching mechanism such as a switch is provided in the surgical operation support apparatus 1, the endoscope or the like, and display is switched using this switch. Also, a user interface for use in switching may be displayed on the output device and display may be switched using the user interface.

[System Configuration]

Figure 3:
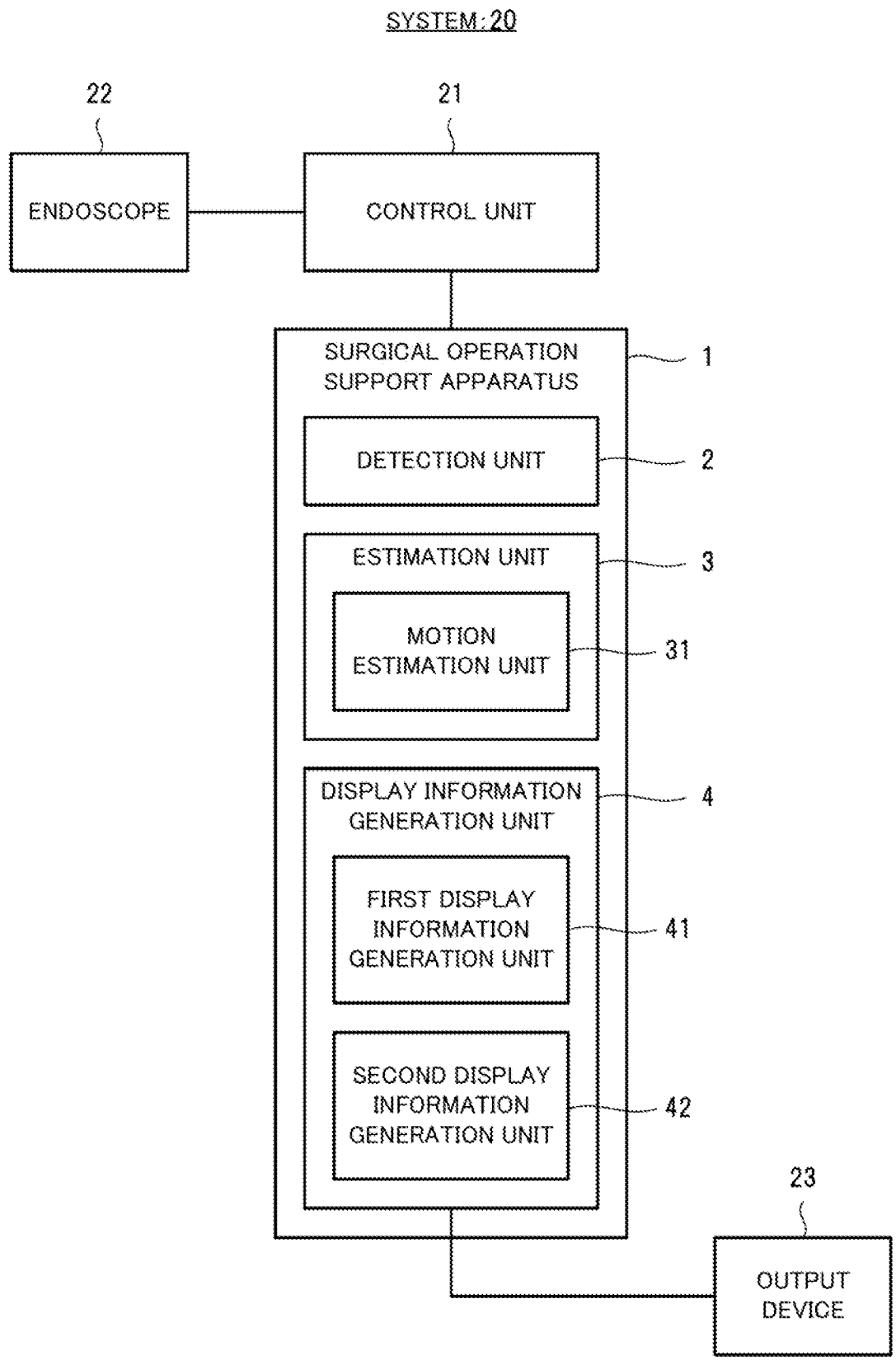
FIG. 3 is a diagram for describing an example of a system having the surgical operation support apparatus.

Next, the configuration of the surgical operation support apparatus 1 in the example embodiment will be described more specifically, using FIG. 3. FIG. 3 is a diagram for describing an example of a system having the surgical operation support apparatus.

As shown in FIG. 3, a system 20 in the example embodiment has a control unit 21, an endoscope 22 and an output device 23, in addition to the surgical operation support apparatus 1. Also, the estimation unit 3 has a motion estimation unit 31. Furthermore, the display information generation unit 4 has a first display information generation unit 41 and a second display information generation unit 42.

The control unit 21 is a video processor, for example, that executes image processing and the like on an input image. Specifically, the control unit 21 acquires an imaging signal from the endoscope 22, performs image adjustment and the like on the imaging signal, generates an image capturing the inside of a living body, and outputs the generated image to the surgical operation support apparatus 1.

The endoscope 22 transmits images of the inside of a living body that capture the inside of a living body such as a human body to the control unit 21 which is connected to the endoscope 22. The endoscope 22 has, for example, an insertion part to be inserted into the body, an image capturing apparatus such as a camera that is provided on the tip side of the insertion part, an operation part for operating bending of the insertion part, image capture of the image capturing part and the like, and a connection part for connecting the endoscope 22 to the surgical operation support apparatus 1. Also, apart from the image capturing apparatus, a lighting part, a nozzle that is used for air supply, water supply and suctioning, a forceps port and the like are provided on the tip side of the insertion part.

The output device 23 acquires information including display information converted into a format that can be output from the display information generation unit 4, and outputs images, audio and the like generated based on this information. Note that the output device 23 includes an image display device that uses liquid crystals, organic EL (ElectroLuminescence) or CRTs (Cathode Ray Tubes), and an audio output device such as a speaker, for example. Note that the output device 23 may also be a printing device such as a printer.

The surgical operation support apparatus will now be specifically described.

The detection unit 2 detects a target site image from the captured image of the inside of the living body. Specifically, the detection unit 2, first, acquires an image captured in time series using the endoscope 22 from the control unit 21. Then, the detection unit 2 detects a region corresponding to the target site (target site image) from the acquired image, using segment processing. Then, the detection unit 2 outputs information indicating the detected target site region to the display information generation unit 4. Information indicating the target site region is conceivably information such as a mask image (black and white binary image) for extracting the target site region, for example.

The estimation unit 3 estimates whether the observer is observing the target site using the target site image displayed on the output device 23. That is, the estimation unit 3 estimates the operating state of the image capturing apparatus which is a camera or the like mounted to the endoscope 22, using one or more images. For example, methods (1) and (2) shown below are conceivable as methods for estimating the operation state.

(1) This method involves calculating the degree of bokeh/blur (first index) of one or more images, and estimating that movement of the image capturing apparatus is small, if the calculated degree of bokeh/blur is smaller than a bokeh/blur threshold set in advance.

(2) This method involves calculating the motion vector of the target site image in a plurality of images (movement amount of target site image: second index) using optical flow processing, and estimating that movement of the image capturing apparatus is small, if the calculated movement amount is smaller than a movement amount threshold set in advance.

Furthermore, the estimation unit 3 may estimate the observation state using one or more images. A method (3) shown below is conceivable as a method for estimating the observation state.

(3) This method involves inputting the degree of image bokeh/blur of the image calculated by (1), or the processing result of optical flow processing calculated by (2), or both thereof into a model for classifying whether observation is being performed, and estimating an estimation result (third index) indicating whether the observer is observing the target site image.

Estimation by (1) will now be specifically described.

In the case of performing estimation by (1), the motion estimation unit 31, first, acquires images captured in time series using the endoscope 22 from the control unit 21. Then, the motion estimation unit 31 calculates a degree of bokeh/blur $\alpha$ using one or more images. Then, the motion estimation unit 31 determines whether the degree of bokeh/blur $\alpha$ is smaller than a bokeh/blur threshold th1. If the degree of bokeh/blur $\alpha$ is smaller than the bokeh/blur threshold th1, the motion estimation unit 31 then estimates that the observer is performing observation. The bokeh/blur threshold th1 is derived by experiment, simulation or the like.

As an example of the method for calculating the degree of bokeh/blur $\alpha$, "Spatial Distribution of Edges" and "Blur" described in 4.1 and 4.4 of the abovementioned Document 2 can be utilized. Specifically, for example, the motion estimation unit 31 calculates a degree of bokeh/blur $\alpha_i$ of an i-th frame image of images captured in time series, using Formula 1.

$$\alpha_i = w_{i,spatial} S_{spatial} + w_{i,blur} S_{blur}, \Sigma_{i,j} w_{i,j} = 1 \quad \text{[Formula 1]}$$

$S_{spatial}$: Score corresponding to Spatial Distribution of Edges $S_{blur}$: Score corresponding to Blur $w_{i,j}$: Weight coefficient of respective scores $\alpha_i$: Degree of bokeh/blur Also, the degree of bokeh/blur α of m number of images of the inside of the living body captured before the target image of the inside of the living body may be utilized based on Formula 2.

$$\alpha_i = \sum_m \gamma^{i-m} \alpha_i \qquad \text{[Formula 2]}$$

$\gamma^{i-m} < 1$ : Forgetting factor

Estimation by (2) will now be specifically described.

In the case of performing estimation by (2), the motion estimation unit 31, first, acquires images captured in time series using the endoscope 22 from the control unit 21. Then, the motion estimation unit 31 extracts the target site image from each image. Then, the motion estimation unit 31 calculates the motion vector of the target site image between images (movement amount u of the target site image) using a plurality of images.

For example, the luminance of a position (x, y) of the target site image captured in time series at a certain time t is given as I(x, y, t). Also, the luminance when this point (x, y) is displaced by (δx, δy) in an image captured an infinitesimal time later t+δt is given as I(x+δx, y+δy, t+δt). Here, Formula 3 holds assuming that the luminance of the corresponding I(x, y, t) and I(x+δx, y+δy, t+δt) of two images described above does not change.

$$I(x,y,t) = I(x+\delta x, y+\delta y, t+\delta t) \qquad \text{[Formula 3]}$$

Next, Taylor expansion is performed for I(x, y, t), assuming that the displacement between images is small. Also, the optical flow constraint equation shown in Formula 4 is obtained, by assuming that higher order terms in the Taylor expansion are negligibly small.

$$I_x u_x + I_y u_y = -I_t \qquad \text{[Formula 4]}$$

$$I_x = \frac{\partial I}{\partial x}, I_y = \frac{\partial I}{\partial y}, I_t = \frac{\partial I}{\partial t}, u_x = \frac{\partial x}{\partial t}, u_y = \frac{\partial y}{\partial t}$$

u in Formula 5 which is represented by $u_x$ and $u_y$ at this time is the motion vector (or optical flow) at the position (x, y) of the target site image.

$$u = [u_x, u_y] \qquad \text{[Formula 5]}$$

Also, various techniques have been proposed for calculating the motion vector u, as described in the abovementioned Document 3. For example, the Lucas-Kanade method assumes that motion vectors are uniform within a local neighborhood, and derives the least squares solution of the motion vectors by imposing the optical flow constraint condition of luminance invariance for each pixel within that neighborhood.

The simultaneous equation shown in Formula 6 can be obtained when considering a neighborhood of m×m=n pixels centered on the target pixel of motion vector estimation.

$$Au = -b, \qquad \text{[Formula 6]}$$

$$\text{where } A = \begin{bmatrix} I_{x_1} & I_{y_1} \\ I_{x_2} & I_{y_2} \\ \vdots & \vdots \\ I_{x_n} & I_{y_n} \end{bmatrix}, u = \begin{bmatrix} u_x \\ u_y \end{bmatrix}, b = \begin{bmatrix} I_{t_1} \\ I_{t_2} \\ \vdots \\ I_{t_n} \end{bmatrix}$$

The motion vector u at this time is calculated as the least squares solution of an evaluation function E.

$$E = \|Au + b\|^2$$

$$A^T A u = A^T (-b),$$

$$u = (A^T A)^{-1} A^T (-b) \qquad \text{[Formula 7]}$$

Then, the motion estimation unit 31 determines whether the calculated movement amount a is smaller than a movement amount threshold th2. If the movement amount a is smaller than the movement amount threshold th2, the motion estimation unit 31 then estimates that the observer is performing observation. The movement amount threshold th2 is derived by experiment, simulation or the like.

Estimation by (3) will now be specifically described.

Figure 4:
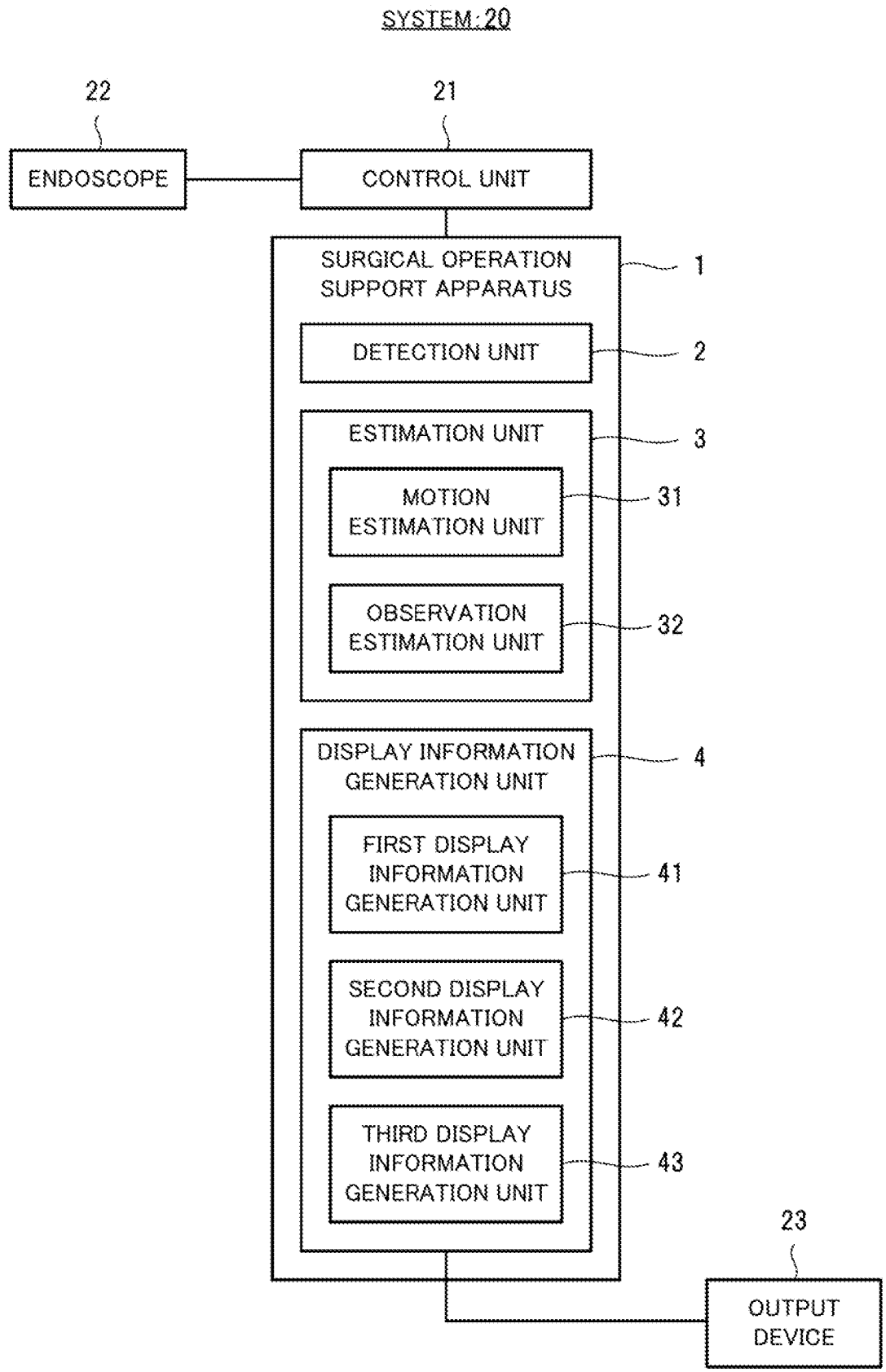
FIG. 4 is a diagram for describing an example of improving switching.

FIG. 4 is a diagram for describing an example of improving switching. In estimation by (3), an index indicating the camera movement, such as the degree of bokeh/blur α estimated by the motion estimation unit 31, or the processing result (movement amount u) of optical flow processing, or both thereof is input into a classification model, and whether the observer is performing observation is estimated.

In the case of performing estimation by (3), the observation estimation unit 32 inputs the degree of bokeh/blur α, or the movement amount u, or both thereof into the classification model, and outputs an estimation result β indicating whether the observer is observing the target site image. The classification model is, for example, a classifier that classifies whether the observer is performing observation. Also, the classification model outputs the likelihood of the observation state as the estimation result β. The estimation result β can be represented by a numerical value from 0.0 to 1.0, for example. The estimation result β is, however, not limited to the abovementioned numerical value.

Specifically, the observation estimation unit 32, first, acquires the estimation result of the motion estimation unit 31, which is the degree of bokeh/blur α, or the movement amount u, or both thereof. Then, the observation estimation unit 32 inputs the estimation result of the motion estimation unit 31 into the classification model. Then, the observation estimation unit 32 outputs the estimation result β, using the classification model. Then, the observation estimation unit 32 determines whether the estimation result β is larger than an observation state threshold th3. If the estimation result β is larger than the observation state threshold th3, the observation estimation unit 32 then estimates that the observer is performing observation. The observation state threshold th3 is derived by experiment, simulation or the like.

The display information generation unit 4 generates display information for performing effective display with respect to the target site image, according to the situation in which the observer is observing the target site image.

If it is estimated that the target site image is being observed, the first display information generation unit 41 generates first display information for facilitating recognition of the target site image. Specifically, the first display information generation unit 41, first, acquires the estimation result (result of (1) or (2) or (3)) from the estimation unit 3. Then, if the estimation result indicates that observation is being performed, the first display information generation unit 41 generates display information for displaying the image 201c having the display 203 such as shown in FIG. 2. Thereafter, the first display information generation unit 41 transmits output information including the generated display information to the output device 23.

In the image 201c in FIG. 2, the display 203 for enabling the observer to observe the target site in detail is performed. As the display 203, it is conceivable to display an outline in a predetermined color on the region of the target site image, for example. However, the display 203 need only be display that enables the position of the target site image to be grasped without inhibiting observation.

If it is estimated to be other than a situation where the target site image is being observed, the second display information generation unit 42 generates second display for facilitating recognition of the target site image. Specifically, the second display information generation unit 42, first, acquires the estimation result (result of (1) or (2) or (3)) from the estimation unit 3. Then, if the estimation result indicates that it is not a situation where observation is being performed, the second display information generation unit 42 generates display information for displaying the image 201b having the display 202 such as shown in FIG. 2. Thereafter, the second display information generation unit 42 transmits output information including the generated display information to the output device 23.

In the image 201b in FIG. 2, the display 202 for enabling the observer to easily grasp the target site image is displayed. The display 202 is conceivably displayed by, for example, filling in the region inside the target site image with a predetermined color or pattern. Also, transparency may be set as the predetermined color. That is, the display 202 may be displayed to be see through.

In the case of switching between the first display and the second display, a third display information generation unit 43 generates one or more third displays to be displayed between the first display and the second display, in order to make the switching appear seamless. The third display is, for example, an intermediate display of the first display and the second display. The intermediate display is, for example, conceivably display obtained by reducing the transparency of the second display, the lower the value of the estimation result β, and by increasing the transparency of the second display, the higher the value of the estimation result β.

Figure 5:
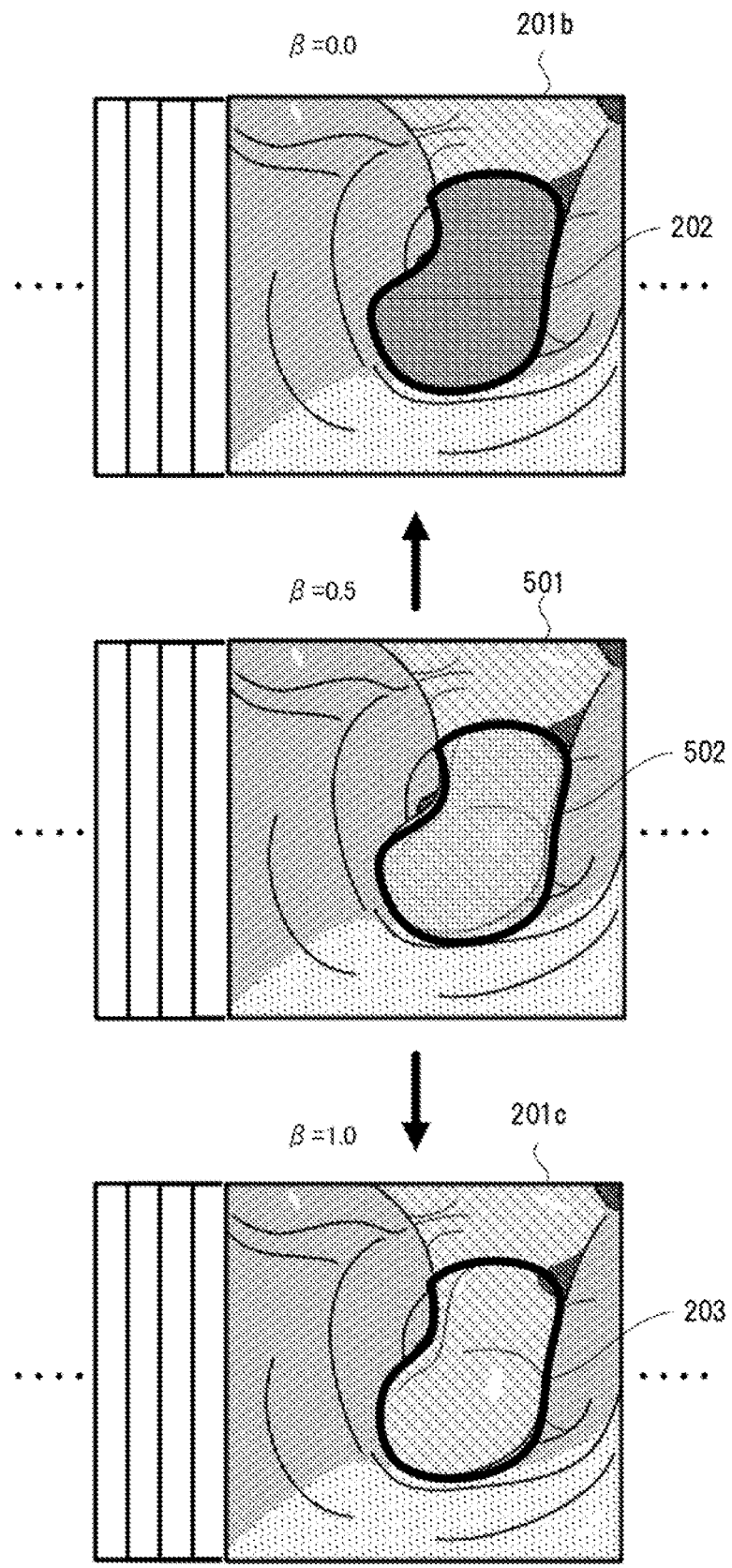
FIG. 5 is a diagram for describing an example of intermediate display.

The third display information generation unit 43 will now be specifically described, using FIGS. 4 and 5.

FIG. 5 is a diagram for describing an example of intermediate display. The third display information generation unit 43, first, acquires the estimation result β from the estimation unit 3. Then, the third display information generation unit 43 generates display information for performing display as shown in FIG. 5, according to the estimation result β. Thereafter, the third display information generation unit 43 transmits output information including the generated display information to the output device 23.

In the example in FIG. 5, the image 201b is displayed if the estimation result β=0.0, an image 501 is displayed if the estimation result β=0.5, and the image 201c is displayed if the estimation result β=1.0. In this way, by changing the display according to the estimation result β, display can be seamlessly changed between the first display and the second display.

In the image 501 of FIG. 5, a display 502 (third display) for enabling the observer to easily grasp the target site image is displayed. The display 502 is conceivably displayed by, for example, filling in the region inside the target site image with a lighter color than the color of the second display. For example, transparency may be set higher than that set for the second display.

[Apparatus Operations]

Figure 6:
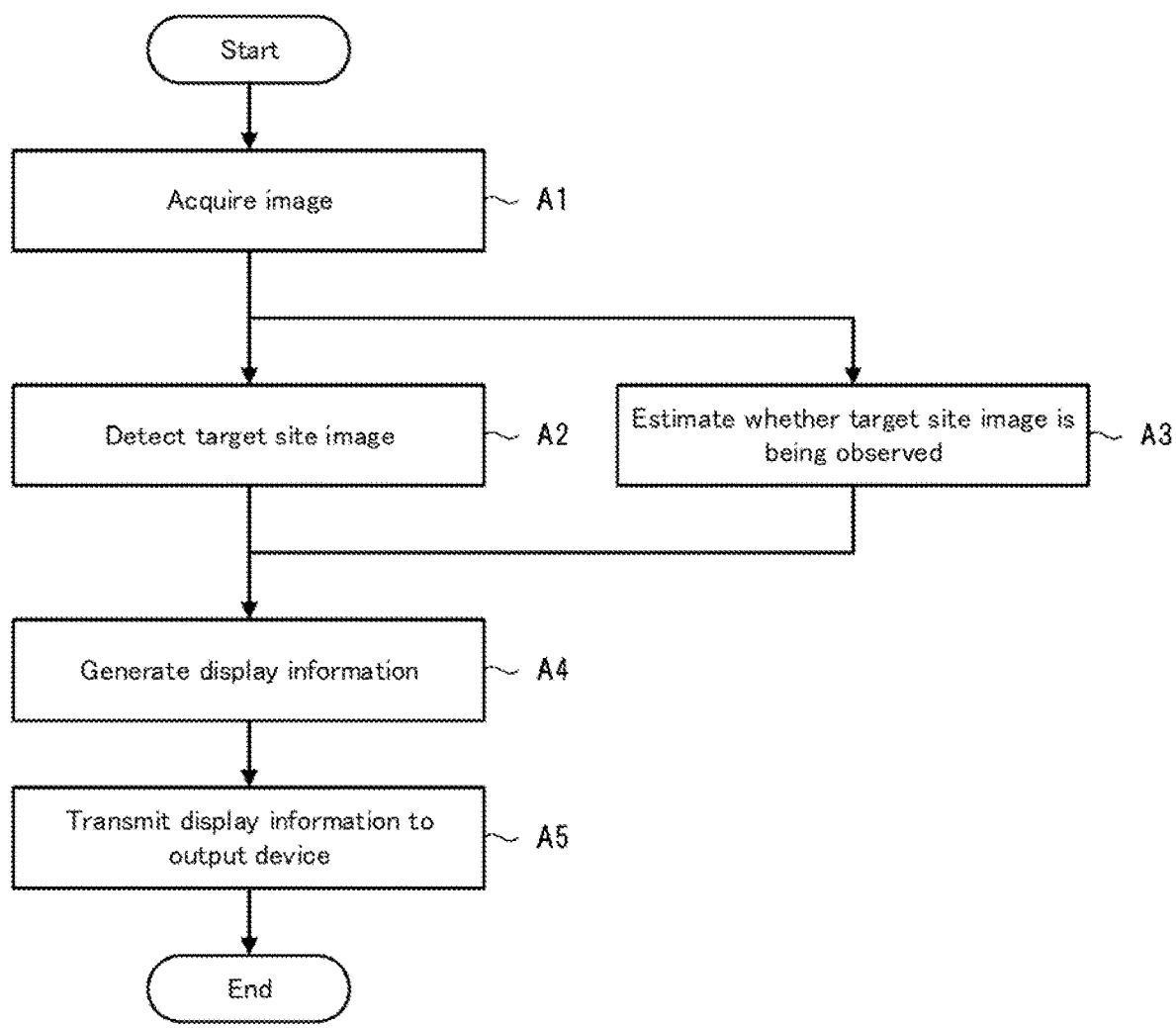
FIG. 6 is a diagram for describing an example of operations of the surgical operation support apparatus.

Next, operations of the surgical operation support apparatus in the example embodiment of the invention will be described using FIG. 6. FIG. 6 is a diagram for describing an example of operations of the surgical operation support apparatus. The following description will refer to FIGS. 1 to 5 as appropriate. Also, in the example embodiment, a surgical operation support method is implemented by operating the surgical operation support apparatus. Therefore, description of the surgical operation support method in the example embodiment is replaced by the following description of the operations of the surgical operation support apparatus.

As shown in FIG. 6, the detection unit 2, first, acquires an image captured in time series using the endoscope 22 from the control unit 21 (step A1). Then, the detection unit 2 detects a region corresponding to the target site (target site image) from the acquired image, using segment processing (step A2). Then, in step A2, the detection unit 2 outputs information indicating the detected target site region to the display information generation unit 4. Information indicating the target site region is conceivably information such as a mask image (black and white binary image) for extracting the target site region, for example.

Also, the estimation unit 3, first, estimates whether the observer is observing the target site using the target site image displayed on the output device 23 (step A3). The abovementioned methods (1), (2) and (3) are conceivable as the estimation method.

(1) This method involves calculating the degree of bokeh/blur (first index) of one or more images, and estimating that movement of the image capturing apparatus is small, if the calculated degree of bokeh/blur is smaller than a bokeh/blur threshold set in advance.

(2) This method involves calculating the motion vector of the target site image in a plurality of images (movement amount of the target site image: second index) using optical flow processing, and estimating that movement of the image capturing apparatus is small, if the calculated movement amount is smaller than a movement amount threshold set in advance.

(3) This method involves inputting the degree of bokeh/blur of the image calculated by (1), or the processing result of optical flow processing calculated by (2), or both thereof into a model for classifying whether observation is being performed, and estimating an estimation result (third index) indicating whether the observer is observing the target site image.

Estimation by (1) will now be specifically described.

In step A3, the motion estimation unit 31, in the case of performing estimation by (1), first, acquires images captured in time series using the endoscope 22 from the control unit 21. Then, in step A3, the motion estimation unit 31 calculates the degree of bokeh/blur α using one or more images. Then, in step A3, the motion estimation unit 31 determines whether the degree of bokeh/blur α is smaller than the bokeh/blur threshold th1. If the degree of bokeh/blur α is smaller than the bokeh/blur threshold th1, in step A3, the motion estimation unit 31 then estimates that the observer is performing observation. The bokeh/blur threshold th1 is derived by experiment, simulation or the like.

Note that the motion estimation unit 31 may correct the degree of bokeh/blur α, by bokeh, blur, tone distribution, hue or contrast or by combining two or more thereof.

Estimation by (2) will now be specifically described.

In step A3, in the case of performing estimation by (2), the motion estimation unit 31, first, acquires images captured in time series using the endoscope 22 from the control unit 21. Then, in step A3, the motion estimation unit 31 extracts the target site image from each image. Then, in step A3, the motion estimation unit 31 calculates the motion vector of the target site image between the images (movement amount a of the target site image). Then, in step A3, the motion estimation unit 31 determines whether the calculated movement amount a is smaller than the movement amount threshold th2. If the movement amount a is smaller than the movement amount threshold th2, in step A3, the motion estimation unit 31 then estimates that the observer is performing observation. The movement amount threshold th2 is derived by experiment, simulation or the like.

Estimation by (3) will now be specifically described.

In step A3, the observation estimation unit 32 inputs the degree of bokeh/blur α, or the movement amount u, or both thereof into a classification model, and outputs the estimation result β indicating whether the observer is observing the target site image. The classification model is, for example, a classifier that classifies whether the observer is performing observation. Also, the classification model outputs the likelihood of the observation state as the estimation result β. The estimation result β can be represented by a numerical value from 0.0 to 1.0, for example. The estimation result β is, however, not limited to the abovementioned numerical value.

In step A3, the observation estimation unit 32, in the case of performing estimation by (3), first, acquires the estimation result of the motion estimation unit 31, which is the degree of bokeh/blur α, or the movement amount u, or both thereof. Then, in step A3, the observation estimation unit 32 inputs the estimation result of the motion estimation unit 31 into the classification model. Then, in step A3, the observation estimation unit 32 outputs the estimation result β using the classification model. Then, in step A3, the observation estimation unit 32 determines whether the estimation result β is larger than the observation state threshold th3. If the estimation result β is larger than the observation state threshold th3, in step A3, the observation estimation unit 32 then estimates that the observer is performing observation. The observation state threshold th3 is derived by experiment, simulation or the like.

Next, the display information generation unit 4 generates display information for performing effective display with respect to the target site image, according to the situation in which the observer is observing the target site image (step A4). Thereafter, the display information generation unit 4 transmits output information including the generated display information to the output device 23 (step A5).

If it is estimated that the target site image is being observed, the first display information generation unit 41, in step A4, generates first display information for facilitating recognition of the target site image. Specifically, in step A4, the first display information generation unit 41, first, acquires the estimation result (result of (1) or (2) or (3)) from the estimation unit 3.

Then, if the estimation result indicates that observation is being performed, the first display information generation unit 41, in step A4, generates display information for displaying the image 201c having the display 203 such as shown in FIG. 2. Thereafter, in step A5, the first display information generation unit 41 transmits output information including the generated display information to the output device 23.

In the image 201c in FIG. 2, the display 203 for enabling the observer to observe the target site in detail is performed. As the display 203, it is conceivable to display an outline in a predetermined color on the region of the target site image, for example. However, the display 203 need only be display that enables the position of the target site image to be grasped without inhibiting observation.

If it is estimated to be other than a situation where the target site image is being observed, the second display information generation unit 42, in step A4, generates a second display for facilitating recognition of the target site image. Specifically, in step A4, the second display information generation unit 42, first, acquires the estimation result (result of (1) or (2) or (3)) from the estimation unit 3.

Then, if the estimation result indicates that it is not a situation where observation is being performed, the second display information generation unit 42, in step A4, generates display information for displaying the image 201b having the display 202 such as shown in FIG. 2. Thereafter, in step A5, the second display information generation unit 42 transmits output information including the generated display information to the output device 23.

In the image 201b in FIG. 2, the display 202 for enabling the observer to easily grasp the target site image is displayed. The display 202 is conceivably displayed by, for example, filling in the region of the target site image with a predetermined color or pattern. Also, transparency may be set as the predetermined color. That is, the display 202 may be displayed to be see through.

Furthermore, in step A4, in the case of switching between the first display and the second display, the third display information generation unit 43 may generate one or more third displays to be displayed between the first display and the second display, in order to make the switching appear seamless.

The third display is, for example, an intermediate display of the first display and the second display. The intermediate display is, for example, conceivably display obtained by reducing the transparency of the second display, the lower the value of the estimation result β, and by increasing the transparency of the second display, the higher the value of the estimation result β.

Specifically, in step A4, the third display information generation unit 43, first, acquires the estimation result β from the estimation unit 3. Then, in step A4, the third display information generation unit 43 generates display information for performing display as shown in FIG. 5, according to the estimation result β. Thereafter, in step A4, the third display information generation unit 43 transmits output information including the generated display information to the output device 23.

In the example in FIG. 5, the image 201b is displayed if the estimation result β=0.0, the image 501 is displayed if the estimation result β=0.5, and the image 201c is displayed if the estimation result β=1.0. In this way, by changing the display according to the estimation result β, display can be seamlessly changed between the first display and the second display.

[Effects of Example Embodiment]

According to the example embodiment as described above, effective display is performed in the case where it is estimated that the observer is observing the target site image, thus enabling observation of the target site image to be facilitated for the observer.

Specifically, as a method for conveying detection results automatically in the case where a surgeon (observer) who is performing an endoscopic surgical operation observes a lesion, display (display 202) that masks the vascular structure of the lesion region inhibits observation of the lesion by the surgeon, and thus display (display 203) indicating the outline of the lesion is desirable. In contrast, in situations other than when observing a lesion, such as in the case of looking for lesions while removing the endoscope or changing the angle of the camera in order to observe a lesion, for example, display (display 202) that enables the position of the lesion to be easily grasped is desirable.

Note that, in the case where the target site image is observed, switching to display that facilitates observation of the target site image may be performed automatically as described above, but a configuration may also be adopted in which the observer is able to switch display manually. For example, a configuration may be adopted in which a switching mechanism such as a switch is provided in the surgical operation support apparatus 1, the endoscope or the like, and display is switched using this switch. Also, a user interface for use in switching may be displayed on the output device and display may be switched using the user interface. Furthermore, audio information relating to audio may be acquired from a microphone, and display may be switched based on the audio information.

[Program]

Figure 7:
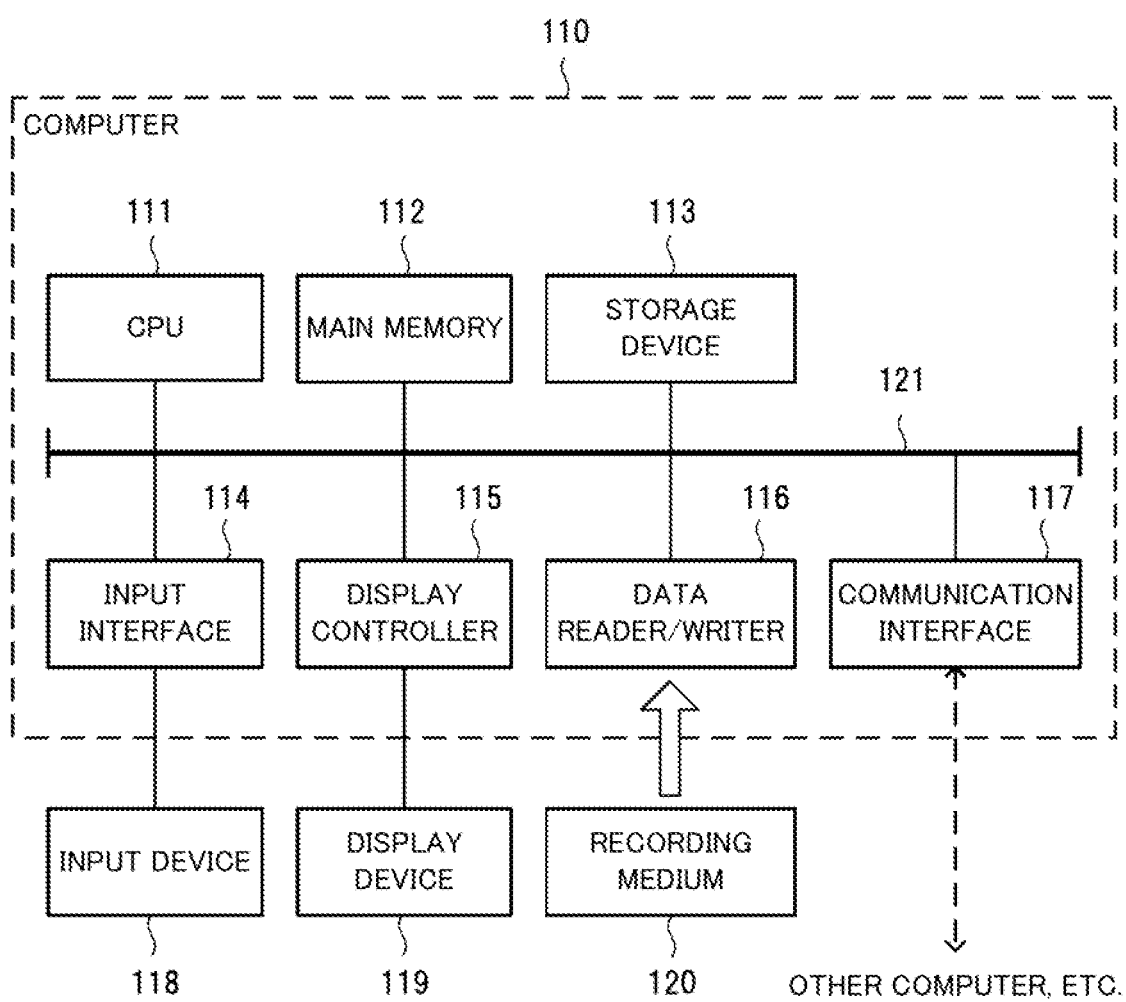
FIG. 7 is a diagram for describing an example of a computer that realizes the surgical operation support apparatus.

A program in the example embodiment of the invention need only be a program for causing a computer to execute steps A1 to A5 shown in FIG. 7. The surgical operation support apparatus and surgical operation support method in the example embodiment can be realized, by this program being installed on a computer and executed. In this case, a processor of the computer functions and performs processing as the detection unit 2, the estimation unit 3 and the display information generation unit 4.

Also, the program in the example embodiment may be executed by a computer system constructed from a plurality of computers. In this case, the computers each function as one of the detection unit 2, the estimation unit 3 and the display information generation unit 4, for example.

[Physical Configuration]

Here, a computer for realizing the surgical operation support apparatus by executing programs of the example embodiment will be described using FIG. 7. FIG. 7 is a diagram for describing an example of a computer for realizing the surgical operation support apparatus.

As shown in FIG. 7, a computer 110 includes a CPU (Central Processing Unit) 111, a main memory 112, a storage device 113, an input interface 114, a display controller 115, a data reader/writer 116 and a communication interface 117. These constituent elements are connected to each other in a data communicable manner, via a bus 121. Note that the computer 110 may include a GPU (Graphics Processing Unit) or an FPGA (Field-Programmable Gate Array), in addition to the CPU 111 or instead of the CPU 111.

The CPU 111 implements various computational operations, by extracting programs (code) of the example embodiment that are stored in the storage device 113 to the main memory 112, and executing these programs in predetermined order. The main memory 112, typically, is a volatile storage device such as a DRAM (Dynamic Random Access Memory). Also, programs of the example embodiment are provided in a state of being stored in a computer-readable recording medium 120. Note that programs of the example embodiment may also be distributed over the Internet connected via the communication interface 117. Note that the recording medium 120 is a non-volatile recording medium.

Also, a semiconductor storage device such as a flash memory is given as a specific example of the storage device 113, other than a hard disk drive. The input interface 114 mediates data transmission between the CPU 111 and input devices 118 such as a keyboard and a mouse. The display controller 115 is connected to a display device 119 and controls display by the display device 119.

The data reader/writer 116 mediates data transmission between the CPU 111 and the recording medium 120, and executes readout of programs from the recording medium 120 and writing of processing results of the computer 110 to the recording medium 120. The communication interface 117 mediates data transmission between the CPU 111 and other computers.

Also, a general-purpose semiconductor storage device such as a CF (Compact Flash (registered trademark)) card or an SD (Secure Digital) card, a magnetic recording medium such as a flexible disk, and an optical recording medium such as a CD-ROM (Compact Disk Read Only Memory) are given as specific examples of the recording medium 120.

Note that the surgical operation support apparatus 1 in the example embodiment is also realizable by using hardware corresponding to the respective constituent elements, rather than by a computer on which programs are installed. Furthermore, the surgical operation support apparatus 1 may be realized in part by programs, and the remaining portion thereof may be realized by hardware.

[Supplementary Notes]

The following supplementary notes are further disclosed in relation to the above example embodiment. While the abovementioned example embodiment can be partially or wholly represented by supplementary notes 1 to 24 described below, the invention is not limited to the following description.

(Supplementary note 1)

A surgical operation support apparatus including:

a detection unit configured to detect a target site image from an image capturing an inside of a living body;

an estimation unit configured to estimate whether the target site image is being observed; and a display information generation unit configured to generate, in a case where it is estimated that the target site image is being observed, a first display for facilitating observation of the target site image.

(Supplementary note 2)

The surgical operation support apparatus according to supplementary note 1, whereby the first display is display indicating, in a predetermined color, a surrounding frame surrounding a contour of the target site image, or a surrounding frame entirely including the target site image, or a surrounding frame surrounding a partial region of the target site image.

(Supplementary note 3)

The surgical operation support apparatus according to supplementary note 1 or 2, whereby the display information generation unit generates, in a case where it is estimated to be other than a situation where the target site image is being observed, a second display for facilitating recognition of the target site image.

(Supplementary note 4)

The surgical operation support apparatus according to supplementary note 3, whereby the second display is display in which a region of the target site image, or a region including the target site image, or a partial region of the target site image is filled in with a predetermined color or pattern.

(Supplementary note 5)

The surgical operation support apparatus according to supplementary note 3 or 4, whereby the display information generation unit generates, in a case of switching between the first display and the second display, one or more third displays to be displayed between the first display and the second display, in order to make the switching seamless.

(Supplementary note 6)

The surgical operation support apparatus according to any one of supplementary notes 1 to 5, whereby the estimation unit estimates whether the target site image is being observed, using a degree of bokeh/blur of the image.

(Supplementary note 7)

The surgical operation support apparatus according to any one of supplementary notes 1 to 6, whereby the estimation unit performs the estimation further using optical flow.

(Supplementary note 8)

The surgical operation support apparatus according to any one of supplementary notes 1 to 7, whereby the estimation unit inputs the degree of bokeh/blur of the image, or a processing result of the optical flow, or both thereof into a model for classifying whether observation is being performed, and estimates whether the target site image in the image is being observed.

(Supplementary note 9)

A surgical operation support method including:

a detection step of detecting a target site image from an image capturing an inside of a living body;

an estimation step of estimating whether the target site image is being observed; and a display information generation step of generating, in a case where it is estimated that the target site image is being observed, a first display for facilitating observation of the target site image.

(Supplementary note 10)

The surgical operation support method according to supplementary note 9, whereby the first display is display indicating, in a predetermined color, a surrounding frame surrounding a contour of the target site image, or a surrounding frame entirely including the target site image, or a surrounding frame surrounding a partial region of the target site image.

(Supplementary note 11)

The surgical operation support method described in supplementary note 9 or 10, whereby, in the display information generation step, in a case where it is estimated to be other than a situation where the target site image is being observed, a second display for facilitating recognition of the target site image is generated.

(Supplementary note 12)

The surgical operation support method according to supplementary note 11, whereby the second display is display in which a region of the target site image, or a region including the target site image, or a partial region of the target site image is filled in with a predetermined color or pattern.

(Supplementary note 13)

The surgical operation support method according to supplementary notes 11 or 12, whereby, in the display information generation step, in a case of switching between the first display and the second display, one or more third displays to be displayed between the first display and the second display are generated, in order to make the switching seamless.

(Supplementary note 14)

The surgical operation support method according to any one of supplementary notes 9 to 13, whereby, in the estimation step, whether the target site image is being observed is estimated, using a degree of bokeh/blur of the image.

(Supplementary note 15)

The surgical operation support method according to any one of supplementary notes 9 to 14, whereby, in the estimation step, whether the target site image is being observed is estimated, using optical flow.

(Supplementary note 16)

The surgical operation support method according to any one of supplementary notes 9 to 15, whereby, in the estimation step, the degree of bokeh/blur of the image, or a processing result of the optical flow, or both thereof is input into a model for classifying whether observation is being performed, and whether the target site image in the image is being observed is estimated.

(Supplementary note 17)

A computer-readable recording medium including a program recorded thereon, the program including instructions for causing a computer to execute:

a detection step of detecting a target site image from an image capturing an inside of a living body;

an estimation step of estimating whether the target site image is being observed; and a display information generation step of generating, in a case where it is estimated that the target site image is being observed, a first display for facilitating observation of the target site image.

(Supplementary note 18)

The computer-readable recording medium according to supplementary note 17, whereby the first display is display indicating, in a predetermined color, a surrounding frame surrounding a contour of the target site image, or a surrounding frame entirely including the target site image, or a surrounding frame surrounding a partial region of the target site image.

(Supplementary note 19)

The computer-readable recording medium according to supplementary notes 17 or 18, whereby, in the display information generation step, in a case where it is estimated to be other than a situation where the target site image is being observed, a second display for facilitating recognition of the target site image is generated.

(Supplementary note 20)

The computer-readable recording medium according to supplementary note 19, whereby the second display is display in which a region of the target site image, or a region including the target site image, or a partial region of the target site image is filled in with a predetermined color or pattern.

(Supplementary note 21)

The computer-readable recording medium according to any one of supplementary notes 19 or 20, whereby, in the display information generation step, in a case of switching between the first display and the second display, one or more third displays to be displayed between the first display and the second display are generated, in order to make the switching seamless.

(Supplementary note 22)

The computer-readable recording medium according to any one of supplementary notes 17 to 21, whereby, in the estimation step, whether the target site image is being observed is estimated, using a degree of bokeh/blur of the image.

(Supplementary note 23)

The computer-readable recording medium according to any one of supplementary notes 17 to 22, whereby, in the estimation step, whether the target site image is being observed is estimated, using optical flow.

(Supplementary note 24)

The computer-readable recording medium according to any one of supplementary notes 17 to 23, whereby, in the estimation step, the degree of bokeh/blur of the image, or a processing result of the optical flow, or both thereof is input into a model for classifying whether observation is being performed, and whether the target site image in the image is being observed is estimated.

Although the instant invention has been described above with reference to an example embodiment, the invention is not limited to the foregoing example embodiment. Various modifications that will be apparent to those skilled in the art can be made to the configurations and details of the instant invention within the scope of the invention.

INDUSTRIAL APPLICABILITY

According to the invention as described above, effective display of a target site image can be performed according to the situation. The invention is useful in fields that require surgical operations using an endoscope.

LIST OF REFERENCE SIGNS

1 Surgical operation support apparatus
2 Detection unit
3 Estimation unit
4 Display information generation unit
20 System
21 Control unit
22 Endoscope
23 Output device
31 Motion estimation unit
32 Observation estimation unit
41 First display information generation unit
42 Second display information generation unit
43 Third display information generation unit
110 Computer
111 CPU
112 Main memory
113 Storage device
114 Input interface
115 Display controller
116 Data reader/writer
117 Communication interface
118 Input device
119 Display device
120 Recording medium
121 Bus

What is claimed is:

1. A surgical operation support apparatus comprising:
a processor; and
a memory storing program code executable by the processor to perform processing comprising:
acquiring images captured in time series by an imaging device mounted on an endoscope;
detecting a target site image by performing segmentation processing on an image captured inside of a living body;
calculating a degree of broken or blur using the acquired images captured in time series using the endoscope;
correcting the calculated the degree of bokeh or blur, by using a distribution of bokeh, blur, tone, hue, or contrast, or by combining two or more of the acquired images captured in time series using the endoscope;
determining whether or not the corrected degree of bokeh or blur is smaller than a bokeh or blur threshold;
when the corrected degree of bokeh or blur is smaller than the bokeh or blur threshold, estimating that an observer is performing observation;
generating, when the target site image has been estimated as being observed by the observer, controlling a display device to superimpose on the acquired images a first display where either a bounding box surrounding a contour of the target site image or a bounding box that includes an entirety of the contour of the target site image; and
when the target site image has not been estimated as being observed by the observer, controlling the display device to superimpose on the acquired image a second display where either a region of the target site image or a region including the target site image is filled with a predetermined color or pattern.

2. The surgical operation support apparatus according to claim 1,
wherein the first display indicates, in a predetermined color, a surrounding frame surrounding the contour of the target site image, a surrounding frame including an entirety the target site image, or a surrounding frame surrounding a partial region of the target site image.

3. The surgical operation support apparatus according to claim 1,
wherein the processor generates, when the target site has not been estimated as being observed by the observed, the second display for facilitating recognition of the target site image.

4. The surgical operation support apparatus according to claim 3,
wherein the processor generates, when switching between the first display and the second display, one or more third displays to be displayed between the first display and the second display, to make the switching seamless.

5. The surgical operation support apparatus according to claim 1,
wherein the processor inputs the degree of bokeh or blur into a model for classifying whether the observer is performing observation, and estimates that the observer is performing observation.

6. The surgical operation support apparatus according to claim 1,
wherein the processor estimates whether the target site image is being observed by the observer, using an optical flow.

7. A surgical operation support method performed by a computer and comprising:
acquiring images captured in time series by an imaging device mounted on an endoscope;
detecting a target site image by performing segmentation processing on an image captured inside of a living body;
calculating the degree of broken or blur using the acquired images captured in time series using the endoscope;
correcting the calculated the degree of bokeh or blur, by using a distribution of bokeh, blur, tone, hue, or contrast, or by combining two or more of the acquired images captured in time series using the endoscope;
determining whether or not the corrected degree of bokeh or blur is smaller than a bokeh or blur threshold;
when the corrected degree of bokeh or blur is smaller than the bokeh or blur threshold, estimating that an observer is performing observation;
generating, when the target site image has been estimated as being observed by the observer, controlling a display device to superimpose on the acquired images a first display where either a bounding box surrounding a contour of the target site image or a bounding box that includes an entirety of the contour of the target site image; and when the target site image has not been estimated as being observed by the observer, controlling the display device to superimpose on the acquired image a second display where either a region of the target site image or a region including the target site image is filled with a predetermined color or pattern.

8. The surgical operation support method according to claim 7, wherein the first display indicates, in a predetermined color, a surrounding frame surrounding the contour of the target site image, a surrounding frame including an entirety the target site image, or a surrounding frame surrounding a partial region of the target site image.

9. The surgical operation support method described in claim 7, comprising:

generating, when the target site has not been estimated as being observed by the observed, the second display for facilitating recognition of the target site image.

10. The surgical operation support method according to claim 9, comprising:

generating, when switching between the first display and the second display, one or more third displays to be displayed between the first display and the second display, to make the switching seamless.

11. The surgical operation support method according to claim 9, comprising:

inputting the degree of bokeh or blur into a model for classifying whether the observer is performing observation, and estimating that the observer is performing observation.

12. A non-transitory computer-readable recording medium storing a program executable by a computer to perform processing comprising:

acquiring images captured in time series by an imaging device mounted on an endoscope;

detecting a target site image by performing segmentation processing on an image captured inside of a living body;

calculating the degree of broken or blur using the acquired images captured in time series using the endoscope;

correcting the calculated the degree of bokeh or blur, by using a distribution of bokeh, blur, tone, hue, or contrast, or by combining two or more of the acquired images captured in time series using the endoscope;

determining whether or not the corrected degree of bokeh or blur is smaller than a bokeh or blur threshold;

when the corrected degree of bokeh or blur is smaller than the bokeh or blur threshold, estimating that an observer is performing observation;

generating, when the target site image has been estimated as being observed by the observer, controlling a display device to superimpose on the acquired images a first display where either a bounding box surrounding a contour of the target site image or a bounding box that includes an entirety of the contour of the target site image; and when the target site image has not been estimated as being observed by the observer, controlling the display device to superimpose on the acquired image a second display where either a region of the target site image or a region including the target site image is filled with a predetermined color or pattern.

* * * * *